United States Patent [19]

Allen

[11] 4,397,845
[45] Aug. 9, 1983

[54] LINCOMYCIN 3-(5'-ADENYLATE) AS ANESTHETIC

[75] Inventor: Harry R. Allen, Texas Township, Kalamazoo County, Mich.

[73] Assignee: The Upjohn Company, Kalamazoo, Mich.

[21] Appl. No.: 379,529

[22] Filed: May 19, 1982

[51] Int. Cl.³ ...................... A61K 31/71; C07H 15/16
[52] U.S. Cl. .................................... 424/180; 536/16.5
[58] Field of Search ............................ 536/16.2, 16.5; 424/180

[56] References Cited

U.S. PATENT DOCUMENTS 3,544,552  12/1970  Argoudelis et al. ............... 536/16.5
3,671,647   6/1972  Argoudelis et al. ............... 536/16.5

Primary Examiner—Johnnie R. Brown
Attorney, Agent, or Firm—Roman Saliwanchik

[57] ABSTRACT

The 3-(5'-adenylate) of lincomycin- and clindamycin-type compounds in which the propyl hygric acid moiety has been replaced by different cyclic amino acids can be used as a local anesthetic in humans and animals.

3 Claims, No Drawings

LINCOMYCIN 3-(5'-ADENYLATE) AS ANESTHETIC

BACKGROUND OF THE INVENTION

The characteristics and preparation of the antibiotic lincomycin are disclosed in U.S. Pat. No. 3,086,912. Clindamycin is disclosed in U.S. Pat. No. 3,496,163. These antibiotics have been extensively used as medicines in humans and animals. A number of patents world-wide have issued concerning these antibiotics and a variety of derivatives thereof.

The structural formulas for lincomycin (1) and clindamycin (2) are shown in Chart 1.

The lincomycin- and clindamycin-type compounds which can be converted to the 3-(5'-adenylate) are shown in Chart 2. In place of the hydroxyl at the three position of the lincosaminide moiety, there is substituted the adenylate residue.

The 3-(5'-adenylate) of the subject invention can be prepared by microbiological transformation procedures. A 3-(5'-adenylate) is shown in Chart 3. This compound, designated U-63,440, is used to exemplify the other compounds which are within the scope of the subject invention, as shown in Chart 2.

BRIEF SUMMARY OF THE INVENTION

Upon administering an effective amount of a compound of the formula as shown in Chart 2 to a human or animal in need of a local anesthetic, the desired anesthetic effect is obtained. An effective amount is recognized as a local anesthetic effective amount. This local anesthetic effect of the compounds of the subject invention is unexpected and surprising since the compounds were previously known only for their antibiotic properties. There is nothing in the prior art which suggests this useful local anesthetic property of the invention compounds.

DETAILED DISCLOSURE OF THE INVENTION

Preparation of the Invention Compounds

The parent compounds disclosed in Chart 2, i.e., those without the adenylate moiety, can be prepared by the procedures disclosed in U.S. Pat. No. 4,278,789.

The required aminosugar starting materials are known in the art. Some of these starting materials can be advantageously prepared by the well known hydrazinolysis of acylamino sugars. The starting materials wherein $R_{12}$ is methyl are disclosed in U.S. Pat. Nos. 4,278,789, 3,702,322, 3,915,954, and 3,502,648. The starting materials wherein $R_{12}$ is ethyl are disclosed in U.S. Pat. Nos. 3,361,628, 3,380,992, 3,502,648, 3,702,322, and 3,915,954. The starting materials wherein $R_{12}$ is 2-hydroxyethyl are disclosed in U.S. Pat. Nos. 3,380,992, 3,817,979, 3,208,996, and 3,915,954. The compounds of this invention wherein $R_{12}$ is

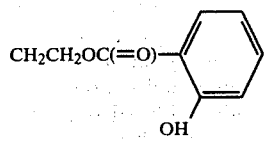

are best prepared by esterifying the appropriate hydroxyl group of the corresponding compound wherein $R_{12}$ is $CH_2CH_2OH$. This esterification can be performed on either the amino sugar of the acylamino sugar and may require protection methods well known in the art.

The 3-(5'-adenylates) of the compounds of Chart 2 can be prepared by following the procedures disclosed in U.S. Pat. No. 3,671,647. Salts of these compounds also can be prepared following the procedures in U.S. Pat. No. 3,671,647.

The dosage range for using the compounds of the subject invention as a local anesthetic is from about 0.05 to about 50 mg/dose. Dosage amount and frequency can be varied as required by the condition of the patient to achieve the desired effect. Compounds of the invention are administered: (1) topically; (2) by direct application to mucous membranes in a suitable dosage form; or (3) by injection for a local effect. Suitable routes of administration are oral, topical, parenteral, and rectal. Thus, suitable dosage forms are oral solutions, suspensions and troches; topical creams, ointments, gels, etc.; parenteral solutions and suspensions; and suppositories.

EXAMPLE 1

Oral Syrup

One thousand cc of an aqueous suspension for oral use, containing in each 5 cc dose 25 mg of U-63,440 is prepared from the following types and amounts of ingredients:

U-63,440—5 gm
Citric acid—2 gm
Benzoic acid—1 gm
Sucrose—700 gm
Tragacanth—5 gm
Lemon oil—2 cc
Deionized water, q.s.—1000 cc The citric acid, benzoic acid, sucrose, tragacanth, and lemon oil are dispersed in sufficient water to make 850 cc of solution. The U-63,440 is stirred into the syrup until uniformly distributed. Sufficient water is added to make 1000 cc.

The composition so prepared is useful as a local anesthetic in adult humans at a dose of 1 tablespoonful (10 cc) 4 times a day.

EXAMPLE 2

Parenteral Solution

A sterile aqueous solution for intramuscular use, containing 10 mg of U-63,440 in 1 cc is prepared from the following types and amounts of materials:

U-63,440—10 gm
Methylparaben—2.5 gm
Propylparaben—0.17 gm
Water for injection, q.s.—1,000 cc The ingredients are dissolved in the water and the solution sterilized by filtration. The sterile solution is filled into vials and the vials sealed.

EXAMPLE 3

Topical Ointment

One thousand gm of 0.25% ointment is prepared from the following types and amounts of ingredients:

U-63,440—2.5 gm
Zinc oxide—50 gm
Calamine—50 gm
Liquid petrolatum (heavy)—250 gm
Wool fat—200 gm
White petrolatum, q.s. 1,000 gm The white petrolatum and wool fat are melted and 100 gm of liquid petrolatum added thereto. The U-63,440, zinc oxide and calamine are added to the remaining liquid petrolatum and the mixture milled until the powders are finely divided and uniformly dispersed. The powder mixture is stirred into the white petrolatum mixture and stirring continued until the ointment congeals.

The foregoing ointment is usefully applied topically to the skin of mammals as a local anesthetic.

The foregoing composition can be prepared by omitting the zinc oxide and calamine.

Following the procedure above, ointments are similarly prepared containing U-63,440 in 0.5, 1, 2, and 5% amounts by substituting 5, 10, 20 and 50 gm of U-63,440 for the 2.5 gm used above.

EXAMPLE 4

Cream

One thousand gm of a cream are prepared from the following types and amounts of ingredients:
U-63,440—50 gm
Tegacid Regular[1]—150 gm
Spermaceti—100 gm
Propylene glycol—50 gm
Polysorbate 80—5 gm
Methylparaben—1 gm
Deionized water, q.s. 1,000 gm

[1]Self-emulsifying glyceryl monostearate from Goldschmidt Chemical Corporation, New York, N.Y.

The Tegacid and spermaceti are melted together at a temperature of 70°–80° C. The methylparaben is dissolved in about 500 gm of water and the propylene glycol, Polysorbate 80, and U-63,440 are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by incorporating 2.5 gm of citric acid and 0.2 g of dibasic sodium phosphate dissolved in about 50 gm of water. Finally, sufficient water is added to bring the final weight to 1,000 gm and the preparation stirred to maintain homogeneity until cooled and congealed.

The foregoing composition is useful as a local anesthetic for humans and animals.

EXAMPLE 5

Ointment, Ophthalmic

One thousand gm of an ophthalmic ointment containing 0.5% U-63,440 are prepared from the following types and amounts of ingredients:
U-63,440—5 gm
Light liquid petrolatum—250 gm
Wool fat—200 gm
White petrolatum, q.s. 1,000 gm The solid ingredients are finely divided by means of an air micronizer and added to the ligh liquid petrolatum. The mixture is passed through a colloid mill to uniformly distribute the micronized particles. The wool fat and white petrolatum are melted together, strained, and the temperature adjusted to 45°–50° C. The liquid petrolatum slurry is added and the ointment stirred until congealed. Suitably the ointment is packaged in one dram ophthalmic tubes.

The foregoing ointment is usefully applied to the eye as a local anesthetic in humans and other animals.

Advantageously the foregoing composition can contain 5 gm (0.5%) of methylprednisolone for the treatment of inflammation.

EXAMPLE 6

Eye-Ear Drops

One thousand cc of a sterile aqueous solution for eye or ear use containing 10 mg of U-63,440 and 5 mg of methylprednisolone in each cc is prepared from the following types and amounts of ingredients:
U-63,440—10 gm
Methylprednisolone phosphate sodium—5 gm
Sodium citrate—4.5 gm
Sodium bisulfite—1 gm
Polyethylene glycol 4000—120 gm
Myristyl-γ-picolinium chloride—0.2 gm
Polyvinylpyrrolidone—1 gm
Deionized water, q.s. and 1000 cc The ingredients are dissolved in the water and the resulting solution is sterilized by filtration. The solution is aseptically filled into sterile dropper containers.

The composition so prepared is useful as a local anesthetic and in the topical treatment of inflammation of the eye and ear as well as other sensitive tissues of the animal body.

EXAMPLE 7

Troches

Ten thousand troches are prepared from the following types and amounts of ingredients:
U-63,440—100 gm
Ethyl aminobenzoate—50 gm
Calcium stearate—150 gm
Powdered sucrose, q.s. 5,000 gm The powdered materials are mixed thoroughly and then compressed into half gram troches following the usual techniques for the preparation of compressed tablets.

The troches are held in the mouth and allowed to dissolve slowly to provide treatment for the mouth and throat of humans.

EXAMPLE 8

Suppository, Rectal

One thousand suppositories, each weighing 2.5 gm and containing 50 mg of U-63,440 are prepared from the following types and amounts of ingredients:
U-63,440—50 gm
Methylprednisolone—1 gm
Ethyl aminobenzoate—75 gm
Zinc oxide—62.5 gm
Propylene glycol—162.5 gm
Polyethylene glycol 4,000 q.s.—2,500 gm The U-63,440, methylprednisolone, ethyl aminobenzoate, and zinc oxide are added to the propylene glycol and the mixture milled until the powders are finely divided and uniformly dispersed. The polyethylene glycol 4000 is melted and the propylene glycol dispersion added slowly with stirring. The suspension is poured into unchilled molds at 40° C.

The composition is allowed to cool and solidify and then removed from the mold and each suppository foil wrapped.

The foregoing suppositories are inserted rectally as a local anesthetic and for local treatment of inflammation.

Alternatively, the foregoing composition can be prepared omitting the steroid.

EXAMPLE 9

Animal Feed

One thousand gm of a feed mix is prepared from the following types and amounts of ingredients:

U-63,440—10 gm
Soybean meal—400 gm
Fish meal—400 gm
Wheat germ oil—50 gm
Sorghum molasses—140 gm The ingredients are mixed together and pressed into pellets. The composition can be fed to laboratory animals, i.e., rats, mice, guinea pigs, and hamsters as a local anesthetic.

For other animals such as poultry, e.g., chickens, ducks, turkeys, and geese, the composition can be added to the animal's regular feed in an amount calculated to give the desired dose of U-63,440.

EXAMPLE 10

Following the procedure of each of the preceding Examples 1-9, inclusive, each local anesthetically active compound of the subject invention is substituted in an equivalent amount for the U-63,440 shown in the example to provide therapeutic properties.

Similarly, each of the above free base compounds can be used in the form of a pharmaceutically (or pharmacologically) acceptable salt, e.g., hydrochloride, sulfate, phosphoric, sodium, potassium, calcium, and lithium.

CHART 1

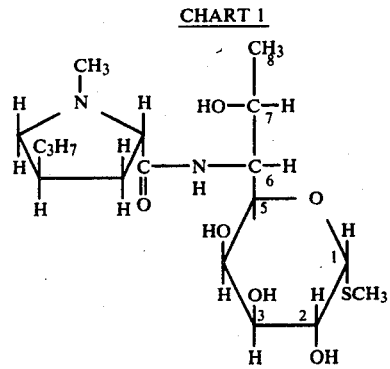

(1)

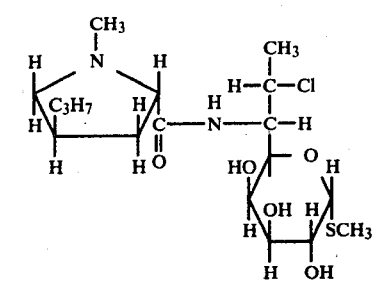

(2)

CHART 2

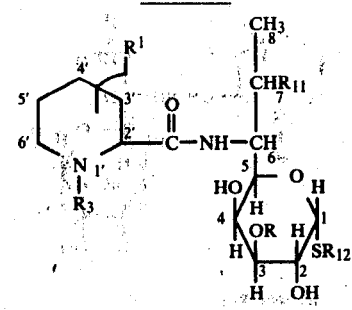

wherein R is

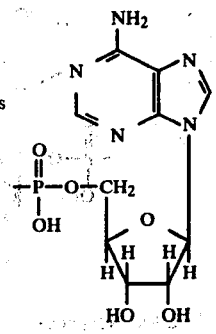

$R_1$ is H, $C_1$-$C_8$—alykl;
$R_{11}$ is OH, OCH$_3$, halogen (Cl, Br, I), —SCH$_2$CH$_2$OH, —SCH$_2$CH$_2$CH$_2$OH, SCH$_3$;

$R_{12}$ is CH$_3$, —CH$_2$CH$_3$, —CH$_2$CH$_2$OH, —CH$_2$CH$_2$OC(=O)— 

CHART 3

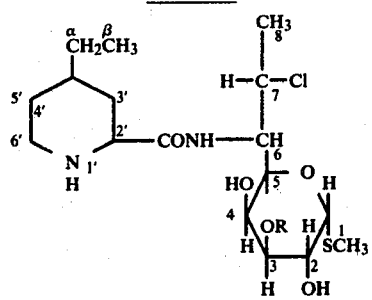

wherein R is

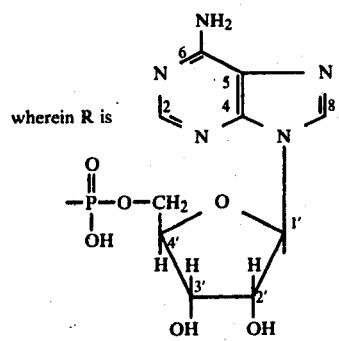

I claim:
1. A method for treating a human or animal subject in need of a local anesthetic which comprises administering to said subject an effective local anesthetic dose of a compound of the formula

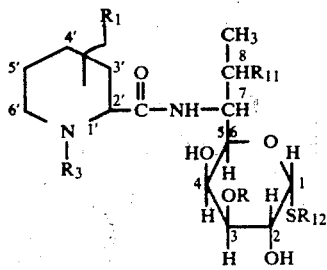

wherein R is

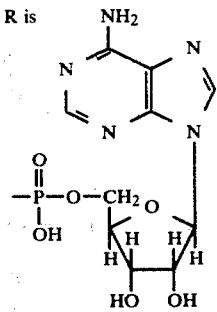

$R_1$ is H, $C_1$–$C_8$-alkyl; $R_{11}$ is OH, $OCH_3$, halogen (Cl, Br, I), $-SCH_2CH_2OH$, $-SCH_2CH_2CH_2OH$, $SCH_3$; $R_{12}$ is $CH_3$, $CH_2CH_3$, $-CH_2CH_2OH$,

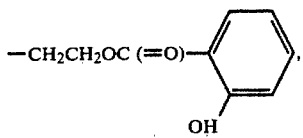

or the pharmaceutically acceptable acid addition salts thereof, selected from the group consisting of hydrochloride, sulfate, phosphoric, sodium, potassium, calcium, and lithium, as an essential active ingredient in combination with a pharmaceutical carrier.

2. A method, according to claim 1, wherein said effective local anesthetic dose is from about 0.05 to about 50 mg/dose.

3. A method, according to claim 1, wherein said administered compound has the formula

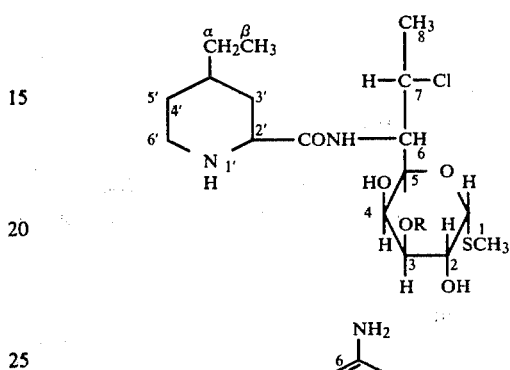

wherein R is

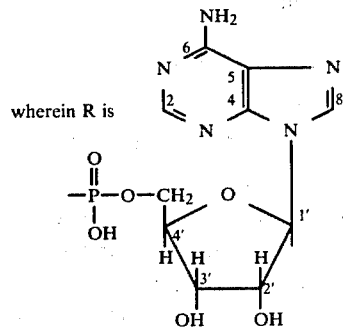

* * * * *